US00PP10920P

United States Patent [19]

Hammond

[11] Patent Number: Plant 10,920

[45] Date of Patent: May 25, 1999

[54] *ARGYRANTHEMUM FRUTESCENS* CULTIVAR NAMED 'GRETEL'

[76] Inventor: Frank Hammond, 100 Boundary Rd., Narre Warren East, Victoria, 3804, Australia

[21] Appl. No.: 08/846,475

[22] Filed: May 1, 1997

[51] Int. Cl.[6] ..... A01H 5/00

[52] U.S. Cl. ..... Plt./68.1

[58] Field of Search ..... Plt./68.1

*Primary Examiner*—Howard J. Locker
*Assistant Examiner*—Kent L. Bell

[57] ABSTRACT

A new and distinct selection of Silver Flower which shall be referred hereinafter as *Argyranthemum frutescens* cultivar 'Gretel'. *Argyranthemum frutescens cultivar Gretal differs distinctively from other Argyranthemum frutescens* plants by its unique combination of deep mauve to pink colored flowers appearing together and a more refined appearance from the dense and short growth habit and small flowers and foliage.

1 Drawing Sheet

BACKGROUND OF THE INVENTION

This invention relates to a new and distinct selection of *Argyranthemum frutescens* (L.) Schultz-Bip, native to the Canary Islands and a member of the compositae family. *Argyranthemum frutescens* cv. 'Gretel' was the result of a controlled breeding program. The seed parent was *Argyranthemum frutescens* cv. 'Blanche' and the pollen parent was *Argyranthemum frutescens* cv. 'Rollasons Red'. I selected this seeding progeny in 1995. My discovery was made at 100 Boundary Road, Narre Warren East, Victoria, Australia. Selection was based on the attributes of the deep mauve to pink colored flowers appearing together and a more refined appearance.

My new plant has been asexually reproduced by cuttings since the discovery in 1995 at 100 Boundary Road, Narre Warren East, Victoria, Australia and later at Monrovia Nursery Company, 18331 E. Foothill Boulevard, Azusa, Calif. Had this controlled hybridization not occured and the seedling not been discovered and propagated, it may have been lost to mankind. It is unlikely these particular select and favorable attributes of this plant could be conveyed to progeny through sexual reproduction in the next generation. However, through extensive propagation by rooting of the plant it has been established that the novel exceptional characteristics of this plant are stable and reliably passed on to clonal specimens through asexual reproduction.

SUMMARY OF INVENTION

*Argyranthemum frutescens* cv. 'Gretel' has a lovely flowering effect with various color tones displayed. Initially the inflorescence opens with ray petals a deep mauve purple. As the inflorescence ages the ray petals fade to a light pink to almost white. The effect is stunning with an overall colorful effect.

The size of my new selection is extremely uniform. The average height of twenty random samples is 31.5 cm with 0.9 cm deviation. This is 9 cm taller than cultivar 'Rollasons Red', the pollen parent which has a deviation of 4.2 cm in height. The seed parent cultivar 'Blanche' is 8 cm shorter, with a deviation of 2.5 cm, however again the parent is not as consistently uniform as my selection. This application is co-pending with those of four other Argyranthemum selections. 'Primrose Petite' (U.S. Plant Patent Application Ser. No. 08/848,790) differs significantly in having yellow ray florets. 'Annabel' (U.S. Plant Patent Application Ser. No. 08/851,475) differs significantly in having white ray florets. 'Blanche' (U.S. Plant Patent Application Ser. No. 08/846, 476) differs significantly in having white ray florets and also in height as previously stated. The final selection 'Carmella' (U.S. Plant Patent Application Ser. No. 08/846,477) differs significantly as outlined below. 'Gretel' has no pink color on the outer basal line whereas 'Carmella' does maintain a pink color band. 'Gretel' has a smaller growth habit whereas 'Carmella' is larger. 'Gretel' has a darker upper surface color and lighter under surface color on the ray florets whereas 'Carmella' has ray florets which are similar in color on the upper and under surfaces. My selection cultivar 'Gretel' has tolerated a minus 5 degree Celsius which is equivalent to a U.S.D.A. hardiness zone seven with no harm or damage. Winter protection is necessary from heavy frost.

BRIEF DESCRIPTION OF ILLUSTRATION

The accompanying photograph shows the plant in flower. The dense heavy bloom virtually covers the foliage. The array of flower colors present at the same time from deep mauve to almost white show the colorful beauty of my selection.

BOTANICAL DESCRIPTION

Below is a detailed description of *Argyranthemum frutescens* cultivar 'Gretel', the color terminology is from the British Horticultural Color Charts. Measurements are based on 20 random samples taken in Australia.

Overall habit: Perennial subshrub.

Overall size: Slightly wider than tall. height 31.5 cm (±0.9 cm). width 45.0 cm (±2.7 cm).

Bloom season in Australia: Heaviest bloom in Spring for 10 weeks. Some flowers present throughout the year. Melbourne: 8 to 10 months per year. Brisbane: 6 to 8 months per year.

*Bloom lastingness.*—7–14 days per inflorescence.

Foliage:

*Arrangement.*—Alternate.

*Surface.*—Upper: glabrous, lightly canescent. lower: glabrous.

*Shape.*—Deeply parted, pinnatisect, primary segments 5.

*Margins.*—Smooth, lobes end with a mucronulate tip.

*Size.*—Length — 45.7 mm (±6.6 mm). width — 25.7 mm (±2.9 mm).

*color.*—Upper leaf surface: Spinach Green 0960/1 and 0960 with sparse covering of Leek green 000858. lower leaf surface: Spinach Green 0960/2.

*Texture.*—Slightly fleshy, succulent.

*Stem coloration.*—Scheeles Green 860, lighter in color than foliage.

Inflorescences:

*Fragrance.*—Faint sweet scent.

*Bud shape.*—Globose.

*Bud length.*—8 mm to 10 mm.

*Bud width.*—6 mm to 8 mm.

*Bud color.*—Spinach Green 0960/3, paper like bracts Mars Orange 013/3 mixed with a tint of Garnet Brown 00918/3.

*Arrangement.*—Heterogamus capitula, 1 per peduncle.

*Peduncle length.*—7 to 10 cm in length.

*Capitulum diameter.*—3.65 cm (±3.3 mm).

*Capitulum height.*—Base of involucre to top of capitulum 11.8 mm (±0.9 mm).

*Disc diameter.*—1.2 cm (±1.1 mm).

*Disc color.*—Chinese Yellow 606.

*Disc floret reproductive organs.*—Pistillate and staminate organs are present.

*Ray floret number.*—Average 16–17.

*Ray floret aspect.*—Flattened, varies from 80 to 100 degrees.

*Ray floret shape.*—Ligulate.

*Ray floret length.*—14–15 mm.

*Ray floret width.*—6–7 mm.

*Ray floret color.*—Initial flowering: Cyclamen Purple 30/3 on upper surface and Cyclamen Purple.1 on under surface. Mature flowering: Cyclamen Purple 30/1, 30/2,30/3. Amaranth Rose 530/3 , 530/1, 530/2, 530/3 upper surface and Amaranth Rose 530/3 on under surface.

*Basal line.*—Fades with age to white.

*Ray floret reproductive organs:.*—Pistillate organs are present.

Fruit: A 2–4 angled cypsela, 1 winged.

Disease resistance: Rust diseases of the genera Coleosporium sp. and Cronartium sp. are not known to occur on this plant in Australia.

I claim:

1. A new and distinct *Argyranthemum frutescens* plant substantially as shown and described which differs distinctively from other *Argyranthemum frutescens* plants by its unique combination of deep mauve to pink colored flowers appearing together and a more refined appearance from the dense and short growth habit and small flowers and foliage.

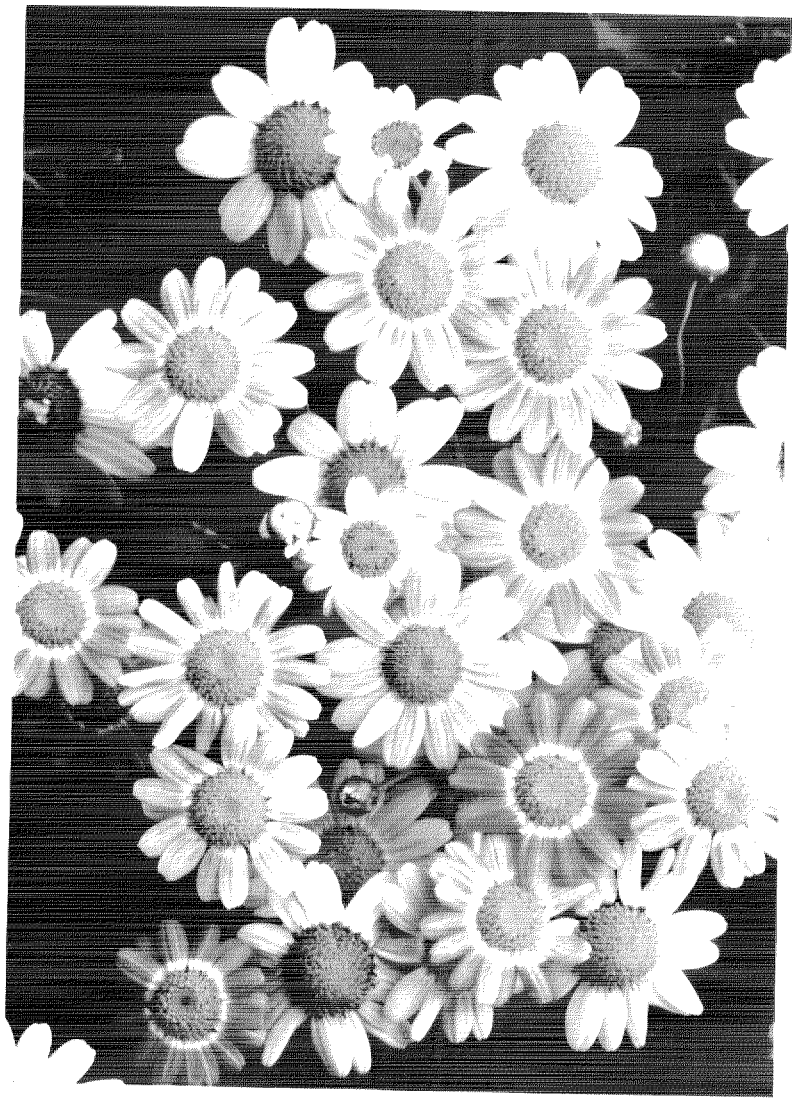

* * * * *